United States Patent [19]

Nakajima et al.

[11] 4,331,762
[45] May 25, 1982

[54] BACILLUS STEAROTHERMOPHILUS STRAIN UK 788 AND PROCESS FOR PRODUCING A USEFUL ENZYME

[75] Inventors: Hiroshi Nakajima, Uji; Kazuhiko Nagata, Nagaokakyo; Masao Kageyama, Uji; Toyohiko Suga; Tadao Suzuki, both of Kyoto; Kenzo Motosugi, Uji, all of Japan

[73] Assignee: Unitika Ltd., Hyogo, Japan

[21] Appl. No.: 209,097

[22] Filed: Nov. 21, 1980

[30] Foreign Application Priority Data

| Apr. 18, 1980 | [JP] | Japan | 55-52198 |
| Apr. 18, 1980 | [JP] | Japan | 55-52199 |
| Apr. 25, 1980 | [JP] | Japan | 55-55647 |
| May 12, 1980 | [JP] | Japan | 55-63180 |
| May 21, 1980 | [JP] | Japan | 55-68018 |
| Jul. 10, 1980 | [JP] | Japan | 55-94868 |

[51] Int. Cl.$^3$ ............... C12N 9/04; C12N 1/20
[52] U.S. Cl. ................... 435/190; 435/41; 435/194; 435/189; 435/232; 435/253; 435/832
[58] Field of Search ............ 435/189, 190, 193, 194, 435/221, 253, 832

[56] References Cited

U.S. PATENT DOCUMENTS

| 3,796,635 | 3/1974 | Delante | 435/832 X |
| 3,826,714 | 7/1974 | Suekane et al. | 435/94 |
| 3,846,239 | 11/1974 | Delante et al. | 435/832 X |
| 3,988,206 | 10/1976 | Shiosaka | 435/832 X |

OTHER PUBLICATIONS

Wright et al., Biochemical Journal, vol. 177, pp. 441–448 (1979).

*Primary Examiner*—Lionel M. Shapiro
*Attorney, Agent, or Firm*—Sughrue, Mion, Zinn, Macpeak & Seas

[57] ABSTRACT

Strain UK 788 (FERM-P No. 5141) that belongs to *Bacillus stearothermophilus*, the cell of which is longer than about 10 microns and which permits easier release of intracellular components than a type culture *Bacillus stearothermophilus*, IAM 11001 is disclosed. Also, a process for producing a useful enzyme selected from the group consisting of a heat-resistant polynucleotide phosphorylase, heat-resistant maleate dehydrogenase, heat-resistant glucokinase, heat-resistant glucose-6-phosphate dehydrogenase and heat-resistant pyruvate kinase by culturing such UK 788 and recovering the desired enzyme from the culture is disclosed. Since the cell of the strain UK 788 is easy to settle and its membrane is also easy to break, the useful enzymes mentioned above can be efficiently produced on an industrial scale.

14 Claims, 2 Drawing Figures

BACILLUS STEAROTHERMOPHILUS STRAIN UK 788 AND PROCESS FOR PRODUCING A USEFUL ENZYME

BACKGROUND OF THE INVENTION

This invention relates to novel microorganism, a biologically pure culture of strain UK 788 of *Bacillus stearothermophilus*, and a process for producing a useful enzyme selected from the group consisting of a heat-resistant polynucleotide phosphorylase, heat-resistant maleate dehydrogenase, heat-resistant glucokinase, heat-resistant glucose-6-phosphate dehydrogenase, and heat-resistant pyruvate kinase.

Since bacterial cells are smaller in size than yeast or fungal cells, they are difficult to collect from a culture, so they are usually collected by centrifugation rather than by filtration. But the rate of sedimentation of cells in centrifugation is proportional to the square of the cell diameter (see Sekiyu Hakko, *Petroleum Fermentation*, p. 102, 1970, Saiwai Publishing Company), so the recovery of bacterial cells from the fermentation broth is more expensive than recovery of yeast and fungal cells and is very disadvantageous in an industrial operation. According to the estimate by Daniel I. C. Wang, the cost of recovery of bacteria is about 3.8 times the cost of recovery of yeast (see *Chemical Engineering*, Vol. 15, p. 99, 1968). Therefore, several methods have been proposed for recovery of bacterial cells and among them is flocculation of cells with a flocculant such as ferric chloride, calcium chloride or polymeric flocculant, or modifying the cell protein to an easily collectable form by heating or treatment with a strong acid or base. These techniques are effective when the cell is not the end product, but when the cell per se or the components in the cell are the end product, they are not effective because the flocculant contaminates the product, or the components in the cell are denatured.

Polynucleotide phosphorylase, one example of the endoenzymes, is used for synthesis of ribo-homopolymers or copolymers of nucleotide, a variety of analog polynucleotides, oligonucleotides having a fixed base arrangement, and for decomposition of RNA. The enzyme also finds much use in the study of the structure and physical properties of nucleic acids. Polynucleotide phosphorylase is conventionally obtained as an extract from *Micrococcus luteus* (see *Procedures in Nucleic Acid Research*, Vol. 2, p. 896, 1971), but the polynucleotide phosphorylase isolated from that microorganism is so labile that it is unsuitable for use even in laboratory-scale research, to say nothing of use on an industrial scale.

Seikagaku (Biochemistry), Vol. 47, p. 738 (1975) describes a method of producing a highly heat-stable, heat-resistant polynucleotide phosphorylase from a thermophilic bacterium *Thermus thermophilus*, and *Nucleic Acids Research*, Vol. 3, p. 219 (1976) describes a method of producing the same enzyme from a thermophilic bacterium *Bacillus stearothermophilus*.

Maleate dehydrogenase which produces oxaloacetic acid from malic acid using nicotinamide adenine nucleotide as a coenzyme has recently been much in demand as an enzyme for use in clinical diagnosis. This enzyme is usually obtained as a purified extract from animal tissues, say, bovine heart (see *Methods in Enzymology*, Vol. 13, p. 99), but maleate dehydrogenase isolated from animal tissues is labile and is not easy to handle. Therefore, a supply of a stable maleate dehydrogenase was desired, and the *Journal of Biological Chemistry*, Vol. 242, p. 1548, 1967 and *Biochemical Journal*, Vol. 177, p. 441, 1979 have described a method of producing a highly heat-stable, heat-resistant maleate dehydrogenase from a thermophilic bacterium *Bacillus stearothermophilus*.

Glucokinase and glucose-6-phosphate dehydrogenase are used to measure the glucose or hexokinase level in the body fluid, which is an important factor in clinical analysis. They are also used to determine the glucose or fructose level in foods which is also an important parameter to know in the manufacture of invert sugar. However, known glucokinase and glucose-6-phosphate dehydrogenase are labile, too (see *Methods in Enzymology*, Vol. 42, pp. 6-39, 1975 ed. by W. A. Wood, and *Advances in Enzymology*, Vol. 48, pp. 97-191, 1979, ed. by Alton Meister). The only known exception is the glucokinase described in *FEBS Letters*, Vol. 37, pp. 212-216, 1973; obtained from a thermophilic *Bacillus stearothermophilus*, this enzyme is heat stable and has long storage stability.

Pyruvate kinase is found in all living tissues such as animals, plants, yeast and bacteria that metabolize carbohydrates by glycolysis or fermentation. In the living cells, the enzyme catalyzes the reaction of forming adenosine triphosphate and pyruvic acid from phosphoenol-pyruvic acid (PEP) and adenosine diphosphate (ADP), so it is used for determination of PEP and ADP. The conventional crystal of pyruvate kinase is available as an isolate from rabbit muscle or swine heart (see *Methods in Enzymology*, Vol. 1, p. 435, and *Journal of Biological Chemistry*, Vol. 234, p. 2428, 1955), but such pyruvate kinase is so labile that it is not suitable for industrial use. Japanese Patent Application (OPI) NO. 9392/78 (the term "OPI" as used herein refers to a "published unexamined Japanese patent application") describes a method of producing a highly heat-stable, heat-resistant pyruvate kinase from a thermophilic *Thermus thermophilus*, and *Seikagaku* (Biochemistry), Vol. 44, p. 649, 1972, describes a method of producing the same enzyme from a thermophilic *Bacillus stearothermophilus*.

To obtain these useful endoenzymes, cultured cells must be first collected by centrifugation or other suitable means before the desired enzyme is extracted from the cells by ultrasonic treatment or physical breaking.

The collection of cultured cells is difficult, as was already mentioned, because of the low specific gravity of bacteria. In addition, bacteria belonging to the genus Bacillus have a relatively hard membrane which can be broken so slightly that the efficiency in extraction of a desired enzyme is low. For these reasons, it has been difficult to produce these enzymes on an industrial scale.

SUMMARY OF THE INVENTION

Therefore, one object of this invention is to provide a thermophilic bacterium having an easily settleable cell and an easily breakable cell wall.

Another object of the invention is to provide a process for industrial large-scale production of a useful enzyme selected from the group consisting of a heat-resistant polynucleotide phosphorylase, heat-resistant maleate dehydrogenase, heat-resistant glucokinase, heat-resistant glucose-6-phosphate dehydrogenase and heat-resistant pyruvate kinase.

To achieve these objects, we conducted a screening of naturally occurring microorganisms by Koch's plate culture (for example, see William Burrows, *Textbook of Microbiology*, 19th Ed., p. 21, W. B. Saunders Company, U.S.A) in search for a thermophilic bacterium having an easily settleable cell and an easily breakable cell wall. As a result, we found a new strain in manure in Ogura, Uji, Kyoto, Japan. In consideration of its properties, the strain is believed to belong to *Bacillus stearothermophilus*, but the cell is extremely elongated and is several to several tens of times larger than the cell of known *Bacillus stearothermophilus* described in *Bergey's Manual of Determinative Bacteriology*. We have found that the new strain is a thermophilic microorganism that contains various useful enzymes and which has an easily settleable cell and an easily breakable cell wall.

Therefore, this invention provides a biologically pure culture of strain UK 788 (FERM-P No. 5141) that belongs to *Bacillus stearothermophilus*, the cell of which is longer than about 10 microns and which permits easier release of intracellular components than a type culture *Bacillus stearothermophilus* IAM 11001. The invention also provides a process for producing a useful enzyme selected from the group consisting of a heat-resistant polynucleotide phosphorylase, heat-resistant maleate dehydrogenase, heat-resistant glucokinase, heat-resistant glucose-6-phosphate dehydrogenase and heat-resistant pyruvate kinase by culturing cells of UK 788 and recovering the desired enzyme from the culture.

The biologically pure culture of strain UK 788 of this invention is very advantageous in industrial use because the cultured cells of the strain can easily be collected and are easy to break. According to this invention, a useful enzyme selected from the group consisting of a heat-resistant polynucleotide phosphorylase, heat-resistant maleate dehydrogenase, heat-resistant glucokinase, heat-resistant glucose-6-phosphate dehydrogenase and heat-resistant pyruvate kinase can be obtained efficiently on an industrial scale.

DETAILED DESCRIPTION OF THE INVENTION

Figure 1:
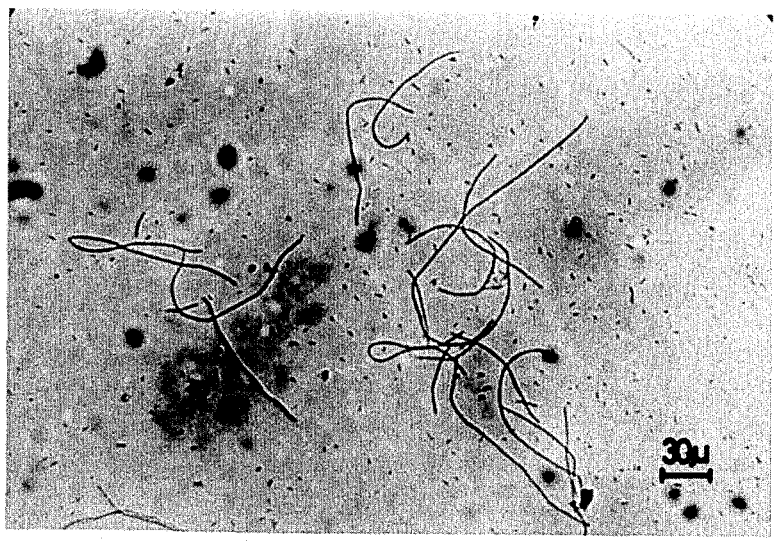
FIG. 1 is a micrograph (150×) of the cells of the strain of this invention and a type culture *Bacillus stearothermophilus* IAM 11001 after culturing on a nutrient agar slant culture at 60° C. for 24 hours.

The mycological properties of a biologically pure culture of strain UK 788 (FERM-P No. 5141) of *Bacillus stearothermophilus* are described below. For the methods and the compositions of media used in the determination of mycological properties, see *The Manual of Microbiological Methods*, 1957, ed. by Society of American Bacteriologists, McGraw-Hill Book Company, *Biseibutsu no Bunrui to Dotei* (Classification and Identification of Microorganisms), 1975, ed. by Takeharu Hasegawa, Tokyo Diagaku Shuppan-Kai, and *Baichigaku Kakuron* (Study of Culture Media), 1967, by Toshiichi Sakazaki, Naya Publishing Company. When an agar medium was used in such determinations, it contained 3 wt% of agar.

Morphological observation: Culture at 60° C. for 24 hours

1. Shape and size of cell: Very long rod, filamentous, 0.8–1.2 × 10 to more than a hundred microns, sometimes more than several hundreds of microns
2. Pleomorphism: None
3. Motility: None
4. Spores: Cylindrical endospores formed in the center or on the tip of the cell. No bulging sporangia.
5. Gram stain: Positive
6. Acid-fast staining: None State of growth: Culture at 60° C. for 24 hours 1. 
   Broth-agar plate culture
   Shape: Circular
   Periphery: Undulate
   Elevation: Flat
   Gloss: None
   Surface: Rough
   Appearance: Semitransparent
2. 
   Broth-agar slant culture
   Growth: Good
   Shape: Filamentous
3. 
   Broth liquid culture
   Surface growth: Slight ring formation
   Turbidity: Strong
   Precipitate: Small
   Coloring and decoloring: None
4. 
   Broth-gelatin stab culture
   A broth containing 30% gelatin was subjected to stab culture at 60° C. for a suitable period, followed by cooling to see if the culture was solidified: Gelatin was liquefied.
5. 
   Broth-gelatin stab culture
   Shape: Beaded
   Surface growth: Good
6. 
   Litmus milk: Litmus discoloration occurred at pH 6.0.
   Milk first solidified, then liquefied.

Physiological properties: Culture at 60° C. for 1 to 2 days

1. Reduction of nitrate: Yes
2. Denitrifying reaction: Negative
3. MR test: Positive
4. VP test: Positive
5. Indole formation: None
6. Hydrogen sulfite formation: None
7. Starch hydrolysis: Yes
8. Utilization of citric acid: None
9. Utilization of nitrate: Yes
10. Utilization of ammonium salt: Yes
11. Pigment formation: None
12. Urease activity: None
13. Oxidase activity: Yes
14. Catalase activity: Yes
15. 
    Growth pH: 5.0–8.5
    Optimum pH: 6.0–7.5
16. 
    Growth temperature: 40°–70° C.
    Optimum temperature: 50°–63° C.
17. 
    Behavior with respect to oxygen: Grows well aerobically and grows slightly even under anaerobic conditions.

18. O-F test: Negative
19. Deamination of phenylalanine: Negative
20. Sodium chloride fastness: Grows with 5% NaCl but cannot grow with 7% NaCl
21. Vitamin requirement: None
22. Tyrosine decomposition: None Formation of acid and gas from carbon source: Culture at 60° C. for 1-2 days.

|     |             | Acid | Gas |
| --- | ----------- | ---- | --- |
| 1.  | L-arabinose | −    | −   |
| 2.  | D-xylose    | +    | −   |
| 3.  | D-glucose   | +    | −   |
| 4.  | D-mannose   | +    | −   |
| 5.  | D-fructose  | +    | −   |
| 6.  | D-galactose | −    | −   |
| 7.  | Maltose     | +    | −   |
| 8.  | Sucrose     | −    | −   |
| 9.  | Lactose     | −    | −   |
| 10. | Trehalose   | +    | −   |
| 11. | D-sorbitol  | −    | −   |
| 12. | D-mannitol  | −    | −   |
| 13. | Innositol   | −    | −   |
| 14. | Glycerin    | −    | −   |
| 15. | Starch      | −    | −   |

These mycological properties generally agreed with those of *Bacillus stearothermophilus* described in *Bergey's Manual of Determinative Bacteriology*, 8th Ed. We therefore compared the strain of this invention with the following type cultures of Bacillus stearothermophilus, IAM 11001, 11002, 11003, 11004 (stored at Institute of Applied Microbiology, The University of Tokyo) and IFO 12550 (stored at Institute for Fermentation, Osaka). The new strain UK 788 differed from the type cultures with respect to two or three physiological properties. The biggest difference is in the size of the cell as is clearly seen from Table 1 and FIG. 1. FIG. 1 is a micrograph (150×) of the cells of new strain UK 788 and type culture IAM 11001 that were subjected to nutrient agar slant culture at 60° C. for 24 hours. In the micrograph, the cell of new strain UK 788 is seen as a much elongated filament, and the cell of the type culture is seen as a dot or short rod.

The strain of this invention has a cell much more elongated than the cell of the type culture of *Bacillus stearothermophilus*, and *Bacillus stearothermophilus* having a cell comparable to the cell of UK 788 is not described in *Bergey's Manual*, loc. cit., or any other reports. We therefore concluded that the strain used in this invention is completely new and named it, as indicated above, *Bacillus stearothermophilus* UK 788 (hereinafter referred to as "FERM-P No. 5141"). The strain was a biologically pure culture and was deposited with the Fermentation Research Institute Agency of Industrial Science and Technology, the Ministry of International Trade and Industry (at No. 1-3, Higashi 1-Chome, Yatabe-Machi, Tsukuba-Gun, Ibaragi, Japan) on August 10, 1979, under a receipt number FERM-P No. 5141.

TABLE 1

| Cell Size of UK 788 (FERM-P No. 5141) and Type Cultures of *Bacillus stearothermophilus* | |
| --- | --- |
| Strain | Cell Size* |
| Strain UK 788 | 0.8–1.2 × 10 to more than a hundred microns, sometimes more than several hundreds of microns |
| IAM 11001 | 0.8–1.0 × 2 to 8 microns |
| IAM 11002 | 0.6–0.8 × 2 to 5 microns |
| IAM 11003 | 0.6–1.0 × 2 to 8 microns |
| IAM 11004 | 0.6–1.0 × 1.5 to 5 microns |
| IFO 12550 | 0.6–1.0 × 2 to 8 microns |

*The figures were those obtained after nutrient agar slant culture at 60° C. for 24 hours.

Common media for cultivation of bacteria may be used in culturing strain FERM-P No. 5141, and a liquid medium is preferred. The medium can contain a variety of nutrient sources: carbon sources include sugars such as glucose, sucrose, fructose, starch hydrolyzate, molasses and sulfite pulp spent liquor, organic acids such as acetic acid and lactic acid, and also alcohols, fats and oils, aliphatic acids, and glycerin that can be assimilated by FERM-P No. 5141; nitrogen sources include inorganic or organic materials such as ammonium sulfate, ammonium chloride, ammonium phosphate, uric acid, ammonia, nitrate, amino acid, peptone, meat extract and yeast extract; inorganic salts such as potassium, sodium, phosphoric acid, zinc, iron, magnesium, manganese, copper, calcium, and cobalt salts. Optionally, traces of metals, corn steep liquor, vitamins, nucleic acid, etc., may also be used. Nutrient sources commonly utilized by bacteria may be used. On a medium containing these nutrient sources, the strain FERM-P No. 5141 of this invention is cultured aerobically for from about 2 to 6 hours, generally at from about 20° to 80° C., preferably at from 40° to 70° C., and more preferably at from 50° to 63° C. Cells containing a heat-resistant acetate kinase can be obtained by either batch culture or continuous culture.

The strain FERM-P No. 5141 of this invention may be used to obtain intracellular components such as sugars, proteins, lipids, nucleic acids and vitamins. Examples of proteins are enzymes and coenzymes; enzymes and coenzymes that are promising as industrial reagents include acetate kinase, ATPase, DNA polymerase, enolase, glucokinase, β-galactosidase, glucose isomerase, lactate dehydrogenase, myokinase, 6-phosphogluconate dehydrogenase, phosphoglycerate kinase, polynucleotide phosphorylase, pyruvate kinase, and superoxide dismutase.

A heat-resistant polynucleotide phosphorylase, heat-resistant maleate dehydrogenase, heat-resistant glucokinase, heat-resistant glucose-6-phosphate dehydrogenase or heat-resistant pyruvate kinase may be produced from strain FERM-P No. 5141 of this invention by either batch cultivation or continuous cultivation. Batch culture is preferably continued to the last stage of the logarithmic growth phase. Continuous culture is preferably conducted by the substance environmental-type continuous cultivation method (chemostat; Herbert D., Ellsworth R. and Telling R. C., *Journal of General Microbiology*, Vol. 14, No. 8, pp. 601–622, 1957) and cells having a high content of the desired useful enzyme can be obtained by adjusting the dilution ratio (the rate of supply of liquid medium to fermentation tank and withdrawal therefrom divided by the volume of liquid medium in the fermentation tank) close to the maximum specific growth rate of FERM-P No. 5141.

A desired useful enzyme can be isolated and purified from the culture by the following procedure: the cells are first collected from the culture by centrifugation or filtration, i.e., the treatment of collecting the cells is industrially carried out by centrifuging the culture with Sharples or De Laval type centrifuge, or by filtering the culture by means of a constant-pressure filtration or a rotating drum filtration (see *Biochemical Engineering,* Second Edition, pages 349 to 355, 1973, ed. by Shuichi Aiba, Arthur E. Humphrey, Nancy F. Millis, University of Tokyo Press), and the collected cells are subjected to a conventional enzyme isolation and purification technique, i.e., the cells are crushed and centrifuged to provide a supernatant which is either fractionated with an organic solvent or a variety of salts such as sodium chloride, magnesium sulfate, ammonium sulfate, sodium sulfate, potassium phosphate, sodium citrate, and so forth, or purified by adsorption on a carrier.

One example of a method for producing a heat-resistant polynucleotide phosphorylase is described in *Nucleic Acids Research,* Vol. 3, p. 219, 1976; an example of a technique for producing a heat-resistant maleate dehydrogenase is described in *Biochemical Journal,* Vol. 177, p. 441, 1979.

One method of producing a heat-resistant glucokinase is described below: cultured cells are suspended in a 50 millimol/l (hereinafter referred to as "mM") phosphate buffer (pH=7.5), in an amount by weight twice as much as the weight of the cells, and the cells are thoroughly crushed with a French press; the cell fragments are removed by centrifugation to provide a crude extract containing glucokinase; the crude extract is dissolved in 500 ml of 3.2 wt% aqueous protamine sulfate and the mixture is thoroughly stirred; the resulting precipitate is removed by centrifugation to provide a protamine supernatant; solid ammonium sulfate is gradually added to the supernatant until it is 50% saturated (4° C.), and the resulting precipitate is collected by centrifugation and again dissolved in 50 mM phosphate buffer (pH=7.5) and desalted by dialysis with 50 mM phosphate buffer (pH=7.5) in 20-times amount per total amounts of the 50 mM phosphate buffer solution of the precipitate; then, the crude extract is passed through a DEAE-Cellulose column equilibrated with 50 mM phosphate buffer (pH=7.5), and upon elution with a solution composed of potassium chloride and a phosphate buffer of the same composition as used above, the desired glucokinase is obtained at an KCl concentration of about 0.13 M or so. Active fractions are combined, concentrated, desalted and passed through a hydroxyapatite column equilibrated with 10 mM phosphate buffer (pH=7.5); upon elution with a phosphate buffer having a linear gradient of from 10 mM to 300 mM, the desired glucokinase is obtained at a concentration of about 120 mM. The active fraction is concentrated and fractionated by column chromatography on Sephadex G-100 using 50 mM tris-HCl buffer (pH=8.0) as an eluting agent.

One example of the method of producing a heat-resistant glucose-6-phosphate dehydrogenase is as follows: cultured cells are suspended in 0.1 M phosphate buffer (pH=7.5) in an amount by weight twice as much as the weight of the cells, and the cells are thoroughly crushed with a French press; the cell fragments are removed by centrifugation to provide a crude extract containing glucose-6-phosphate dehydrogenase; 600 ml of the crude extract is dissolved in 300 ml of 1 wt% aqueous protamine sulfate and the mixture is thoroughly stirred; the resulting precipitate is removed by centrifugation to provide a protamine supernatant; solid ammonium sulfate is gradually added to the supernatant until it is 50% saturated (4° C.), and the resulting precipitate is collected by centrifugation and again dissolved in 0.1 M phosphate buffer (pH=7.5) and desalted by dialysis with 0.1 M phosphate buffer (pH=7.5) in 20-times amount per total amounts of the 0.1 M phosphate buffer solution of the precipitate; then, the crude extract is passed through a DEAE-Cellulose column equilibrated with 20 mM phosphate buffer (pH=7.5) containing 2 mM mercaptoethanol and 2 mM sodium ethylenediaminetetraacetate, and upon elution with a solution composed of potassium chloride and a buffer of the same composition as used above, the desired glucose-6-phosphate dehydrogenase is obtained at an KCl concentration of about 0.15 M. Active fractions are combined, concentrated, desalted and passed through a hydroxyapatite column equilibrated with 5 mm phosphate buffer (pH=7.5); upon elution with a phosphate buffer having a linear gradient of from 5 mM, to 250 mM, the desired glucose-6-phosphate dehydrogenase is obtained at a concentration near 75 mM. The active fraction is concentrated, desalted and fractionated by column chromatography on ultrogel ACA 34 using an eluting agent composed of 50 mM tris-HCl buffer containing 0.1 M potassium chloride. The active fraction is then passed through a DEAE-Sephadex A-50 column equilibrated with 30 mm phosphate buffer (pH=7.7) containing 2 mM mercaptoethanol and 2 mM sodium ethylenediaminetetraacetate, and eluted with a buffer solution (of the same composition as above) plus potassium chloride having an KCl linear gradient of 0.1 M.

One example of a method of producing a heat-resistant pyruvate kinase is described in *Seikagaku (Biochemistry),* Vol. 44, p. 649, 1972.

These useful enzymes obtained can be purified by the techniques described above, and the physicochemical properties of the resulting crystals and the mechanism of their actions can be compared with those of the crystals obtained from other strains of *Bacillus stearothermophilus;* the heat-resistant polynucleotide phosphorylase obtained according to the present invention has the same properties as the one described in *Nucleic Acids Research,* Vol. 3, p. 219, 1976, the heat-resistant maleate dehydrogenase obtained according to the present invention has the same properties as the one described in *Biochemical Journal,* Vol. 177, p. 441, 1979; the heat-resistant glucokinase obtained according to the present invention has the same properties as the one described in *FEBS Letters,* Vol. 37, p. 212, 1973; and the heat-resistant pyruvate kinase obtained according to the present invention has the same properties as the ones described in *Seikagaku (Biochemistry),* 44, p. 649, 1972 and Japanese Patent Application (OPI) No. 9392/78.

The physicochemical properties of the crystal of the heat-resistant glucose-6-phosphate dehydrogenase and the mechanism of its action are specifically described below.

The heat-resistant glucose-6-phosphate dehydrogenase according to this invention is a glucose-6-phosphate wherein the maximum residual activity of the enzyme, when treated in a buffer at about 50° C. for about 15 minutes, can be maintained at about 80% or more, preferably about 90% or more, and more preferably about 100%, based on the original activity. The concentration and pH of the buffer are not limited to particular values, and generally, the concentration is between 5 mM and 500 mM, and the pH is between 7 and 10.5. For the purposes of this invention, 100 mM tris-HCl buffer (pH=ca. 9.0) containing 100 mM potassium chloride is preferred.

1. Activity

The glucose-6-phosphate dehydrogenase catalyzes a reaction represented by the following scheme:

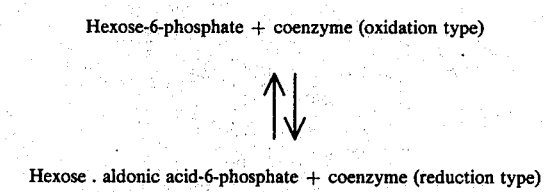

Hexose-6-phosphate + coenzyme (oxidation type)

⇅

Hexose . aldonic acid-6-phosphate + coenzyme (reduction type)

In these schemes, the hexose-6phosphate is a generic term for glucose-6-phosphate, mannose-6-phosphate and galactose-6-phosphate, and the hexose-aldonic acid-6-phosphate is a generic term for gluconic acid-6-phosphate, mannoic acid-6-phosphate and galactonic acid-6phosphate. The coenzyme is either NADP or NAD.

2. Substrate specificity

The glucose-6-phosphate has a Michaelis constant (Km value) of about 0.16 mM. The reaction rates for a given concentration of substrates mannose-6-phosphate and galactose-6-phosphate are about 40% and 20%, respectively, of the rate for glucose-6-phosphate. The Km values for coenzymes NADP and NAD are about 0.016 mM and 1.64 mM, respectively.

3. Optimum pH

About 9.0 (at 30° C.)

4. Stable pH range

Little inactivation occurs at a pH of 7.0 to 10.5 even if the enzyme is treated at 4° C. for 24 hours.

5. Temperature range suitable for exhibiting enzyme activity

The activity increases with a temperature increase from 25° to 75° C. at a pH of 8.9. In most cases, the enzyme is used to catalyze the reaction at 30° C.

6. Heat resistance

The enzyme is stable against heating at 57° C. for 15 minutes.

7. Molecular weight

Gel chromatography on Sephacryl S-200 showed that the enzyme had a molecular weight of about 230,000. The glucose-6-phosphate dehydrogenase from yeast or *Leuconostoc mesenteroides* had a molecular weight of about 100,000 in the same analysis.

8. Determination of enzyme activity

To a mixture of 2 mM glucose-6-phosphate, 0.5 mM NADP, and 5 mM magnesium chloride in 50 mM tris-HCl buffer (pH=8.9), a suitable amount of glucose-6-phoshate dehydrogenase was added, and the activity of the enzyme was determined on the basis of the increase in the absorbance at 340 nm of NADP reduction type (H) for a given time. The activity required to increase the absorbance of 1 micromol of NADPH at 340 nm per minute was defined to be one unit. A purfied glucose-6-phosphate dehydrogenase had an activity of about 100 units per mg (of purified enzyme) at 30° C. Since the glucose-6-phosphate dehydrogenase of this invention is highly heat-resistant, it is capable of catalyzing the desired reaction at a temperature between about 50° and 60° C., at which the previously used glucose-6-phosphate dehydrogenase is inactivated. The activity in that temperature range is even higher.

9. Purity

In a disc electrophoresis in 7.5% acrylamide at pH 9.4, the purified product of the glucose-6-phosphate dehydrogenase moved to the positive electrode and gave a single band. In SDS electrophoresis, the enzyme also moved to the positive electrode and gave a single band.

10. Compositional analysis

The proportions of the amino acids in the glucose-6-phosphate dehydrogenase are set forth below:

Aspartic acid 11.04%, threonine 5.24% serine 4.56%, glutamic acid 11.86%, proline 3.66%, glycine 6.67%, alanine 7.92%, cystine (cysteine) 0.62%, valine 6.09%, methionine 1.97%, isoleucine 5.59%, leucine 8.04%, tyrosine 3.72%, phenylalanine 4.88%, lysine 5.28%, histidine 3.40%, arginine 6.56%, tryptophan 2.72%

11. Crystalline structure

The glucose-6-phosphate dehydrogenase has yet to be crystallized, so its crystalline structure has not been determined.

The cells of FERM-P No. 5141 cultured and harvested by the method of this invention are very easy to collect, and the centrifugation time, that was 10 minutes at 8,000 G with the known strains of *Bacillus stearothermophilus*, is reduced to about a fifth thereof. This offers a great merit because it permits so far impractical cell collection by filtration through a filter medium. The cells of the known *Bacillus stearothermophilus* required 15 minutes of ultrasonic treatment (Frequency: 10 KHz, Output: 200 W) to break, but the collected cells of FERM-P No. 5141 can be equally broken by an ultrasonic treatment that lasts for only about 3 minutes under the same conditions. This also presents a significant advantage in the industrial production of a heat-resistant polynucleotide phosphorylase, heat-resistant maleate dehydrogenase, heat-resistant glucokinase, heat-resistant glucose-6-phosphate dehydrogenase and heat-resistant pyruvate kinase.

This invention is now described in greater detail by reference to the following examples which are given here for illustrative purposes only and are by no means intended to limit the scope of the invention.

EXAMPLE 1 AND COMPARATIVE EXAMPLE 1

A 500-ml conical flask was charged with 100 ml of a medium prepared by dissolving in one liter of tap water a mixture of 2 g of glucose, 2 g of $(NH_4)_2SO_4$, 1 g of yeast extract (Difco), 1 g of $KH_2PO_4$, 1 g of $Na_2HPO_4.12H_2O$ and 0.1 g of $MgSO_4.7H_2O$, closed up with a cotton stopper and sterilized with pressurized steam (121° C., 1 atm.) for 10 minutes. The medium was cooled to 50° C. and inoculated with *Bacillus stearothermophilus* UK 788 (FERM-P No. 5141) grown on a nutrient agar slant medium of the same formulation as indicated above, and subjected to rotary shake cultivation in a rotary shaker (RGR No. 2 type shaker of Takasaki Seisakusho, 180 rpm) at 55° C. After conducting the rotary shake cultivation for 5 hours, when the growth of cells was observed, the turbidity of the medium had an absorbance of 0.1 at 660 nm (measured by 101 type spectrometer produced by Hitachi, Ltd.) and the growth of cells entered the last stage of the logarithmic growth phase, the cultivation was stopped and the cells were collected by centrifugation with a centrifuge (RS 71 of Tomy Seisakusho) for 2 minutes at 8,000 G. The yield of cells collected was determined. One gram of the wet cells was suspended in 20 ml of 0.1 M phosphate buffer (pH 7.0) and the protein that leaked from the cells treated with an ultrasonic breaker (Model 200 M of Kubota Medical Appliance Supply Corp.) was measured.

In Comparative Example 1, the procedure of Example 1 was repeated, except that *Bacillus stearothermophilus* IAM 11001 was used.

It was confirmed that the cells of FERM-P No. 5141 could be recovered from the culture medium by centrifugation more easily than the cells of IAM 11001; the percent recovery of FERM-P No. 5141 was 98% and that of IAM 11001 was 42%.

Figure 2:
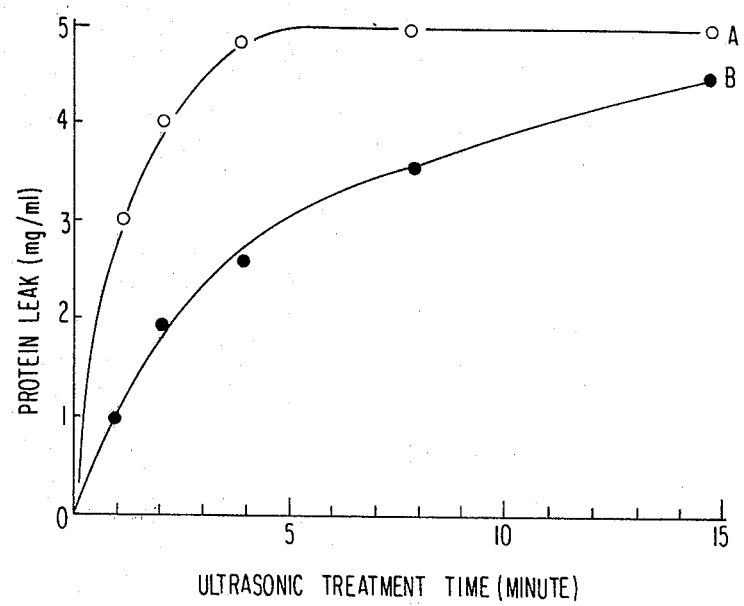
FIG. 2 is a graph showing the relation between ultrasonic treatment time and protein leak, i.e., a graph showing a degree of a breaking tendency of the bacterial cell.

FIG. 2 represents the relation between ultrasonic treatment time and protein leak. In the figures, curve A represents Example 1 and curve B represents Comparative Example 1. As is clear from FIG. 2, the cells used in Example 1 could be broken and intracellular protein leaked by an ultrasonic treatment required only about a fifth of the period required to break the cells used in Comparative Example 1. The protein leak was determined by the biuret method (see Gornall A. G., *Journal of Biological Chemistry*, Vol. 177, p. 751, 1949).

EXAMPLE 2

Culture was performed in ten 500-ml conical flasks using a medium of the same composition as used in Example 1. The liquid cultures were combined, transferred to a 30-liter jar fermentor (MSJ-U Model of Marubishi Rika Sochi, using a straight impeller turbine) that contained 20 liters of a medium of the same composition and which had been sterilized with pressurized steam (121° C., 1 atm., 15 minutes), and subjected to fermentation at 60° C. and 400 rpm with air supplied at a rate of 20 liters/min. Cell growth was soon observed and a drop in pH occurred. The fermentation was continued for another 3 hours while 4 N NaOH was used to maintain the pH at 6.5. When the cell growth entered the last stage of the logarithmic growth phase, the culture was stopped and the medium was continuously centrifuged with a centrifuge (LAPX 202 of Alpha Laval) at 8,000 G for 2 minutes, to provide 120 g of wet cells in a yield of 97%. In the same manner as in Example 1, the relation between the ultrasonic treatment time and intracellular protein leak was examined, and the relative ratio of protein leaked upon a 3-minute treatment was 90%, indicating that the strain FERM-P No. 5141 had easily settleable cells and an easily breakable cell wall even after bench-scale fermentation.

EXAMPLE 3

The liquid cells brokne by ultrasonic treatment in Example 1 contained 1,500 U of heat-resistant polynucleotide phosphorylase per mg of wet cells (1.5 U per mg of protein). This figure was substantially equal to the level of heat-resistant polynucleotide phosphorylase in the cells obtained in Comparative Example 1. The level of heat-resistant polynucleotide phosphorylase was determined by chlorimetric analysis of phosphoric acid freed from adenosine diphosphate when oligoadenosine was used as a primer (*Nucleic Acids Research*, Vol. 3, p. 219, 1976). The enzymatic activity required to free 1 micromol of phosphoric acid per hour was defined to be one unit (hereunder referred to as U).

EXAMPLE 4

The level of heat-resistant polynucleotide phosphorylase in the wet cells produced in Example 2 was determined as in Example 3, and it was found to be 1,700 U per gram of wet cells (1.6 U per mg of protein).

EXAMPLE 5

Batch culture was performed in a 30-liter jar fermentor in the same manner as in Example 2. When the cell growth entered the last stage of the logarithmic growth phase and the residual glucose level in the liquid culture was less than 0.01 wt%, a chemostatic fermentation was performed with the dilution ratio being held close to the maximum specific growth rate of the microorganism by supplying a fresh medium (of the same composition as used in Example 1) to the fermentor and withdrawing the fermentation liquor from the fermentor with a metering pump at a rate of 24 liters per hour. The other culture conditions were as follows: temperature, 60° C.; pH, 6.8–7.0 (controlled automatically with 4 N NaOH), air supply rate, 20 liters per min; and stirring speed, 600 rpm. During the fermentation, foaming occurred, so a defoaming agent (KM-70 of Shinetsu Chemical Industry Co., Ltd.) was added. Throughout the continuous fermentation that lasted for about 4 hours, the cell concentration was maintained at the level achieved at the start of the fermentation (5.8 g of wet cells per liter or 0.75 g of dry cell per liter), and 550 g of wet cells were centrifuged from 96 liters of the fermentation liquor. The cells so obtained contained 1,900 U of heat-resistant polynucleotide phosphorylase per gram of wet cells (1.8 U per mg of protein). The cells harvested by continuous fermentation contained more heat-resistant polynucleotide phosphorylase per unit cell than those produced solely by batch processing.

EXAMPLE 6

To the solution containing broken cells that was obtained by ultrasonic treatment in Example 1, 0.6 wt% of protamine sulfate was added to precipitate nucleic acids which were then removed by centrifugation at 8,000 G for 10 minutes. The resulting supernatant or crude enzyme extract contained 0.05 U of heat-resistant maleate dehydrogenase per mg of protein, which figure was substantially equal to the activity of heat-resistant maleate dehydrogenase in the cells produced in Comparative Example 1 (0.06 U/mg of protein).

The level of heat-resistant maleate dehydrogenase was determined by the method described in *Journal of Biological Chemistry*, Vol. 242, p. 1548, 1967: changes in oxaloacetic acid are converted to changes in nicotinamide adenine dinucleotide reduction type (hereunder referred to as NADH), and these changes are traced by measuring the absorbance at 340 nm, and the enzymatic activity required to reduce the absorbance of 1 micromol of NADH at 340 nm per minute is defined to be one unit (hereunder referred to as U).

EXAMPLE 7

The cells of FERM-P No. 5141 were cultured and collected in the same manner as in Example 5. The level of heat-resistant maleate hydrogenase contained in 1 g of the wet cells was determined as in Example 6, and it was found to be 0.09 U per mg of protein. The cells harvested by continuous fermentation contained more heat-resistant maleate dehydrogenase per unit cell than those produced by batch process.

EXAMPLE 8

The solution containing broken cells that was obtained by an ultrasonic treatment in Example 1 contained 9.5 U of a heat-resistant glucokinase per gram of wet cells (0.12 U per mg of protein), which figure was substantially equal to the level of heat-resistant glucokinase in the cells produced in Comparative Example 1.

EXAMPLE 9

The wet cells obtained in Example 2 contained 10.3 U of heat-resistant glucokinase per gram of wet cells (0.13 U per mg of protein).

EXAMPLE 10

The wet cells obtained by repeating the procedure of Example 5 contained 12.8 U of heat-resistant glucokinase per gram of wet cells (0.16 U per mg of protein). The cells harvested by continuous fermentation contained more heat-resistant glucokinase per unit cell than those produced solely by batch processing.

EXAMPLE 11

The solution containing broken cells that was obtained by ultrasonic treatment in Example 1 contained 3.9 U of a heat-resistant glucose-6-phosphate dehydrogenase per gram of wet cells (0.14 U per mg of protein), which figure was substantially equal to the level of heat-resistant glucose-6-phosphate dehydrogenase in the cells produced in Comparative Example 1.

EXAMPLE 12

The wet cells obtained in Example 2 contained 4.2 U of a heat-resistant glucose-6-phosphate dehydrogenase per gram of wet cells (0.17 U per mg of protein).

EXAMPLE 13

The wet cells obtained by repeating the procedure of Example 5 contained 4.8 U of a heat-resistant glucose-6-phosphate dehydrogenase per gram of wet cells (0.2 U per mg of protein). The cells harvested by continuous fermentation contained more heat-resistant glucose-6-phosphate dehydrogenase per unit cell than those produced by batch process.

EXAMPLE 14

The solution containing broken cells that was obtained by ultrasonic treatment in Example 1 contained 34.7 U of a heat-resistant pyruvate kinase per gram of wet cells (0.44 U per mg of protein), which figure was substantially equal to the level of heat-resistant pyruvate kinase in the cells produced in Comparative Example 1. The level of heat-resistant pyruvate kinase was determined by measuring the decrease in the absorbance at 340 nm of nicotinamide adenine dinucleotide reduced form (NADH) that was used to reduce pyruvic acid freed from PEP upon transfer of a phosphate group to ADP. The enzymatic activity required to reduce the absorbance of 1 micromol of NADH at 340 nm per minute was defined to be one unit (hereunder referred to as U).

EXAMPLE 15

Wet cells of FERM-P No. 5141 were produced as in Example 2, and the level of heat-resistant pyruvate kinase in the cells was determined as in Example 14, and it was found to be 37.6 U per gram of wet cell (0.48 U per mg of protein).

EXAMPLE 16

Wet cells of FERM-P No. 5141 were produced as in Example 5, and the level of heat-resistant pyruvate kinase in the cells was determined as in Example 14, and it was found to be 46.4 U per gram of wet cell (0.59 U per mg of protein). The cells harvested by continuous fermentation contained more heat-resistant pyruvate kinase per unit cell than those produced solely by batch processing.

While the invention has been described in detail and with reference to specific embodiments thereof, it will be apparent to one skilled in the art that various changes and modifications can be made therein without departing from the spirit and scope thereof.

What is claimed is:

1. A biologically pure culture of strain FERM-P No. 5141 of *Bacillus stearothermophilus*, the cell of which is longer than about 10 microns and which permits easier release of an intracellular component than a standard strain *Bacillus stearothermophilus* IAM 11001.

2. A process of extracting an intracellular component from strain FERM-P No. 5141, comprising culturing cells of strain FERM-P No. 5141 of *Bacillus stearothermophilus* and recovering the desired intracellular component from the culture.

3. A process for producing a useful enzyme selected from the group consisting of a heat-resistant polynucleotide phosphorylase, heat-resistant maleate dehydrogenase, heat-resistant glucokinase, heat-resistant glucose-6-phosphate dehydrogenase and heat-resistant pyruvate kinase comprising culturing cells of strain FERM-P No. 5141 of *Bacillus stearothermophilus* and recovering the desired enzyme from the culture.

4. A process according to claim 3, wherein the culture is performed by a batch process until the cell growth gas entered the last stage of the logarithmic growth phase.

5. A process according to claim 4, wherein continuous culture is performed with a dilution ratio held close to the maximum specific growth rate of a biologically pure culture of strain FERM-P No. 5141.

6. A process as in claim 3 or 4, wherein the culturing is conducted in a liquid medium.

7. A process as in claim 6, wherein the culturing is conducted in a liquid medium.

8. A process as in claim 3 or 4, wherein the culturing is conducted aerobically for from about 2 to 6 hours at a temperature of from about 20° to 80° C.

9. A process as in claim 8, wherein the temperature is from 40° to 70° C.

10. A process as in claim 8, wherein the temperature is from 50° to 63° C.

11. A process as in claim 2, wherein the intracellular component is a protein and an enzyme.

12. A process as in claim 6, wherein the culturing is conducted aerobically for from about 2 to 6 hours at a temperature of from about 20° to 80° C.

13. A process as in claim 12, wherein the temperature is from 40° to 70° C.

14. A process as in claim 12, wherein the temperature is from 50° to 63° C.

* * * * *